United States Patent
Beilfuss et al.

(10) Patent No.: US 7,045,542 B1
(45) Date of Patent: May 16, 2006

(54) LOW-TEMPERATURE-STABLE PRESERVATIVES

(75) Inventors: Wolfgang Beilfuss, Hamburg (DE); Ralf Gradtke, Tornesch (DE); Olaf Kramf, Quickborn (DE); Andreas Teevst, Bad Bramst (DE)

(73) Assignee: Air Liquide Sante (International), Paris Cedex (FR)

( * ) Notice: Subject to any disclaimer, the term of this patent is extended or adjusted under 35 U.S.C. 154(b) by 735 days.

(21) Appl. No.: 10/110,475

(22) PCT Filed: Oct. 17, 2000

(86) PCT No.: PCT/IB00/01489

§ 371 (c)(1),
(2), (4) Date: Apr. 12, 2002

(87) PCT Pub. No.: WO01/28332

PCT Pub. Date: Apr. 26, 2001

(30) Foreign Application Priority Data

Oct. 20, 1999 (DE) ................................ 199 51 328

(51) Int. Cl.
*A01N 43/52* (2006.01)
*A01N 25/02* (2006.01)
*A01N 25/22* (2006.01)

(52) U.S. Cl. ...................... 514/395; 514/772; 514/937; 514/970; 514/971

(58) Field of Classification Search ................ 514/395, 514/970, 971, 772, 937
See application file for complete search history.

(56) References Cited

FOREIGN PATENT DOCUMENTS

| | | |
|---|---|---|
| EP | 0 031 454 A2 | 7/1981 |
| EP | 0 351 195 A2 | 1/1990 |
| GB | 2 066 075 | 7/1981 |
| WO | 99/55505 | 11/1999 |

*Primary Examiner*—John Pak
(74) *Attorney, Agent, or Firm*—Young & Thompson

(57) ABSTRACT

A liquid, cold-temperature-stabilized preservative is based on carbendazim or a salt thereof, which includes, as low-temperature stabilizer, at least one aromatic alcohol and/or at least one aromatic glycol ether and/or a pyrrolidone.

17 Claims, No Drawings

LOW-TEMPERATURE-STABLE PRESERVATIVES

This application is a 371 of PCT/IB00/01489, filed on Oct. 17, 2000.

The invention relates to liquid low-temperature-stable preservatives stable at low temperatures for industrial preservation, in particular for long-lasting protection in water-based products and for imparting biocidal properties to objects or coatings whose surfaces, as experience shows, are frequently attacked by fungi. It further relates to a process for the preparation and use thereof.

Fungal attack is not only visually unappealing, but can, in the case of subsequent growth of lichen or moss, also lead to material damage and a reduction in service life. The attack of objects or coatings applied thereto occurs particularly intensively in areas of high atmospheric humidity, such as, for example, in the food industry sector, in dairies, breweries or on the north faces of buildings. In particular, coatings such as paints, varnishes and renders are affected.

The attempt to solve the above-described problem by adding pulverulent substances to the coating materials used is associated with numerous application disadvantages. The demand for solvent-free or low-solvent preparations led to the development of aqueous dispersions in which known, water-insoluble fungicidal active ingredients were used.

For example, aqueous dispersions based on carbendazim and other active ingredients have been found although, because of the fact that the fungicide carbendazim is sparingly soluble, they are not very stable upon prolonged storage and at relatively high and relatively low temperatures and, in numerous fields of use (e.g. in the cutting fluid sector) cannot be incorporated clearly and homogeneously into the products to be furnished. After standing for a relatively long period precipitates form which are difficult to disperse or cannot be dispersed at all.

To avoid this problem, salts of carbendazim have been used, for example alkylbenzenesulphonate salts thereof, preferably in organic solvents, such as 1,2-propylene glycol.

However, such compositions comprising carbendazim salts likewise displayed the tendency towards precipitations during preparation, storage or transportation. The precipitations occurred at room temperature, but also sometimes only at relatively low temperatures (e.g. +4° C.) or in winter during frost (e.g. at −5° C.). These precipitations are in turn irreversible at low temperatures, i.e. they do not disappear again when room temperature is reached.

The object of the present invention is therefore to render preservatives comprising carbendazim or carbendazim salts stable at low temperatures, it being the aim that this low-temperature stability extends below minus temperatures such as, for example, −5° C., and is retained over a relatively long period, even during storage at such low temperatures.

Surprisingly, the object according to the invention was then achieved by the fact that we have found that stable, homogeneous, low-temperature-stable liquid products based on carbendazim or carbendazim salts can be prepared if the composition comprises, as low-temperature stabilizer, at least one aromatic alcohol and/or at least one aromatic glycol ether and/or at least one pyrrolidone, even small amounts sufficing to obtain this low-temperature stability.

The aromatic alcohols or glycol ethers also improve the antimicrobial/germicidal or preserving action of the preparations, and they are, in particular, antimicrobially active in the vapour phase.

The liquid, low-temperature-stabilized preservative based on carbendazim or a salt thereof according to the invention is therefore characterized in that it comprises, as low-temperature stabilizer, at least one aromatic alcohol or aromatic glycol ether or a pyrrolidone.

Preferred embodiments are the subject of the dependent claims.

Preferred low-temperature stabilizers according to the invention are the aromatic alcohols phenylpropanol and benzyl alcohol and the $C_6$–$C_{10}$-aryloxy-$C_2$–$C_6$-alkylene glycol ethers classed as aromatic glycol ethers, where the aryl group is, in particular, a phenyl group and independently thereof the alkylene group is, in particular, a $C_2$- or $C_3$-alkylene group.

Particularly preferred low-temperature stabilizers are phenoxypropanols and phenoxyethanol, the phenoxypropanols including 1-phenoxy-3-propanol, 2-phenoxy-1-propanol and 1-phenoxy-2-propanol. Very particular preference is given to phenoxyethanol and mixtures of 2-phenoxy-1-propanol and 1-phenoxy-2-propanol (referred to in the examples as "phenoxypropanols").

Also suitable are pyrrolidones, N-methyl-pyrrolidone and N-octylpyrrolidone being preferred.

These stabilizers can, for example, be used in exchange or partial exchange for solvents or dispersants used hitherto, such as, for example, 1,2-propylene glycol.

The content of the claimed low-temperature stabilizer in preservatives according to the invention is at least 2% by weight, preferably at least 3% by weight and in particular at least 5% by weight, the maximum content being noncritical if there is complete exchange for media used hitherto. The low-temperature stabilizer according to the invention can be present, for example, in an amount of 10, 15 and 20% by weight, but also of 70, 80 or 90%. It fulfils then not only the function of the low-temperature stabilizer, but also that of the solvent or solubility promoter.

In preferred embodiments, a salt of carbendazim is present in the liquid low-temperature-stabilized preservative according to the invention, preference being given to the alkylbenzenesulphonate salts which have 6 to 18, in particular 10 to 14 and preferably 12, carbon atoms in the alkyl group. A particularly preferred alkylbenzenesulphonate salt of carbendazim is carbendasulf, which can be prepared by reacting carbendazim with dodecylbenzenesulphonic acid (Marlon AS 3-acid) in propylene glycol at about 85° C. The hydrochloride and the hydrobromide of carbendazim are also suitable salts according to the invention.

Because of the higher stability even at low temperatures, the content of fungicide in the preservative remains on a high level, as a result of which biocidal action can likewise be maintained for a long period.

Moreover, because of the possibility of considerably lowering or avoiding the content of diverse solvents and other low-temperature stabilizers, a reduction in the preparation costs of carbendazim-containing products can be achieved.

Therefore, because of the higher low-temperature stability, the preservatives according to the invention have the following advantages over comparable products of the prior art:

more stable liquid concentrate,
more stable product at low temperature,
more cost-effective preparation,
purer product,
more effective product,
alkali-stable active ingredient,
temperature-stable active ingredient,
comparatively inexpensive (e.g. compared with BIT),
combination with known biocidal active ingredients is possible,
use for imparting antimicrobial properties to materials is favourable,
sufficiently resistant to washing out,
sufficiently colour-stable, discoloration-stable.

The low-temperature stabilizers according to the invention can be used subsequently to or even during the preparation of, for example, the alkylbenzenesulphonates of carbendazim, such as, for example, carbendasulf, as additive, partial replacement or complete replacement of solvents used hitherto, such as, for example, 1,2-propylene glycol etc. This has the advantage that the reaction time and temperature for the preparation of the clear homogeneous solution can be reduced, as a result of which a higher thermal stress ("roasting") is avoided, which contribute to the decomposition of the alkylbenzenesulphonates. Also as a result of the avoidance of such additional thermal stress, the content of alkylbenzenesulphonate remains comparatively high again and the type and amount of the decomposition products decreases.

The preservatives according to the invention can be used as additives for coatings, for plastic dispersions, in particular those which are film-forming and are based, for example, on polyacrylate, for the treatment of surfaces and materials and for imparting fungicidal properties to paints, varnishes and renders, for container preservation and for material protection and for the preservation of metalworking fluids (concentrates and emulsions).

In combination with further active ingredients, including, for example, algicides and bactericides, the activity spectrum of the preservatives according to the invention can also be extended to further areas.

In practice, the use concentration of the preservative according to the invention in the material to be preserved can be in the range from 0.01 to 10% by weight, in particular 0.05 to 5% by weight and preferably 0.15 to 3% by weight. In coatings, the preservative according to the invention can be used in amounts such that, on an area of 1 m$^2$, 0.01 to 10 g, preferably 4 g, are used.

In addition to carbendazim or carbendazim salts such as carbendasulf, the preservatives according to the invention can comprise other biocidal active ingredients (bactericidal, fungicidal, algicidal and/or virucidal). This produces broad-activity, sometimes synergistically active, products.

Examples of such biocidal active ingredients which may be present in the preservatives according to the invention are
- isothiazolones, such as N-octylisothiazolone (e.g. Kathon 893=45% N-octylisothiazolone in 1,2-propylene glycol), 5-chloro-N-methylisothiazolone and N-methylisothiazolone (e.g. Kathon 886 salt-containing mixture of 5-chloro-N-methylisothiazolone and N-methylisothiazolone), benzisothiazolone, 4,5-dichloro-N-octylisothiazolone, Promexal, N-butyl-BIT and others,
- aldehydes or aldehyde donor compounds, such as, for example, formaldehyde, glutaraldehyde, o-phthal-aldehyde, ethylene glycol bishemiformal, propylene glycol hemiformal, butyl glycol hemiformal, diethylene glycol butyl ether hemiformal, benzyl alcohol hemiformal, Grotan Bk, Mar 71, Grotan WS, dimethyldimethylolhydantoin (DMDMH), Protectol 140, dimethylolurea, N-methylolchloroacetamide, Dowicil 200, sodium hydroxymethylglycinate,
- organohalogen compounds, such as IPBC, dibromo-dicyanobutane (DBDCB), chloroacetamide, Bronopol, Amical 48, trichlorocarbanilide,
- sulphur-containing compounds, such as 2-mercapto-pyridine N-oxide and salts thereof (e.g. Pyrion-Na) or complex compounds (e.g. zinc pyrithione), pyrion disulphide, TCMTB, Preventol VPOC 3061, tetramethylthiuram disulphide, 3,5-dimethylthiadiazinethione, methylene bisthiocyanate, thiabendazole,
- active oxygen compounds, such as t-butyl hydroperoxide,
- phenols and salts thereof, such as p-chloro-m-cresol, p-chloro-m-xylenol, o-phenylphenol, o-benzyl-4-chlorophenol, parabens, Irgasan DP 300,
- algicides, such as Diuron, Terbutyn, Prometryn, Irgarol 1051,
- N-cyclohexyldiazenium dioxide or salts or complexes, such as the K salt, Al complex, Lonzabac 12 and others,
- cation-active ingredients, such as benzalkonium chloride (solid and 50% strength aqueous solution), cetylpyridinium salts, dodecylguanidine or salts thereof, chlorhexidine salts, octenidine salts, laurylpropylenediaminequanidinium acetate, Vantocil IB and others.

Examples are given below which are intended to illustrate the invention, without signifying any limitation.

By way of example, additives suitable for improving the stability of carbendasulf-containing preparations are described.

The improvement in the stability of carbendasulf-containing preservatives (e.g. low-temperature stability) is possible as a result of the addition of aromatic alcohols or aromatic glycol ethers (5 to 15% of benzyl alcohol, phenoxyethanol, phenoxypropanols).

EXAMPLE 1

Preparation of Preservatives with Various Stabilizers

4% by weight of carbendazim and 6.5% by weight of Marlon AS 3 (amounts given are based on the total weight) were heated in 1,2-propylene glycol to 85° C. After the temperature was reached, the mixture was left to cool to about 60° C. and filtered. The remaining constituents were added to the filtrate, and the mixture was stirred for about 15 minutes. Following seeding with carbendasulf crystals, the mixture was stored in clear glass at −5° C.

Following storage for about 3 months at −5° C. the ranking of the low-temperature stabilization (replacement of 1,2-propylene glycol as previously used solvent for 10% or 15% of stabilizer according to the invention) is as follows:

3-phenylpropanol>phenoxypropanols>N-methyl-pyrrolidone>dipropylene glycol monomethyl ether>1,2-propylene glycol.

After about 15½ months at −5° C. the mixtures have the following precipitate percentages:

| Formulations | Solvent or stabilizer | % Precipitate | |
|---|---|---|---|
| 1 | 1,2-Propylene glycol | (without stabilizer 80%) | |
| | | with 10% stabilizer | with 15% stabilizer |
| 2, 3 | N-Methylpyrrolidone | 30% | 15% |
| 4, 5 | 3-Phenylpropanol | 10% | <5% |
| 6, 7 | Dipropylene glycol monomethyl ether | 50% | 40% |
| 8, 9 | Phenoxypropanols | 20% | 0% |

Result: An addition of selected stabilizers significantly improves the low-temperature stability of carbendasulf-containing preservatives (control without stabilizer is formulation 1). The improvement compared with 1,2-propylene glycol or dipropylene glycol monobutyl ether is apparent in the case of 10 or 15% phenoxypropanol from a reduction in the amount of precipitate from 50 to 20% or 40 to 0% respectively, and in the case of 10 or 15% 3-phenylpropanol from a reduction in the amount of precipitate from 40 to 10% or 40 to <5% respectively. In the case of N-methylpyrrolidone, a reduction from 50 to 30 and from to 15% respectively is found.

EXAMPLE 2

Preparation of Preservatives with Various Stabilizers

Carbendazim, Marlon AS 3 and propylene glycol (constituents 1 to 3; see table) were heated together to 85° C. with stirring. After this temperature had been reached, the mixture was left to cool to about 60° C. and filtered (very little insoluble matter). The filtrate was combined with the mixture of constituents 4 to 8 (see table) and stirred for about 4 of an hour. After seeding, the examples are stored in clear glass at −5° C., 4° C., 25° C. or 40° C. The results are given in the table below ("Zonenfex" is a salt-free solution of a mixture of 5-chloro-N-methylisothiazolone and N-methylisothiazolone in glycol derivatives):

| No. | 14.4.1997 | A | B | C | D | E |
|---|---|---|---|---|---|---|
| 1 | Carbendazim | 4.0 | 4.0 | 4.0 | 4.0 | 4.0 |
| 2 | Marlon AS 3 | 6.5 | 6.5 | 6.5 | 6.5 | 6.5 |
| 3 | Propylene glycol | 40.0 | 40.0 | 40.0 | 40.0 | 40.0 |
| 4 | Zonenfex | 1.0 | 1.0 | 1.0 | 1.0 | 1.0 |
| 5 | Kathon 893 (?) | 17.0 | 17.0 | 17.0 | 17.0 | 17.0 |
| 6 | Phenoxyethanol | | 10.0 | 15.0 | | |
| 7 | Phenoxypropanols | | | | 10.0 | 15.0 |
| 8 | Propylene glycol | 31.5 | 21.5 | 16.5 | 21.5 | 16.5 |
| | Appearance 14.04.97 | Clear solution | Clear solution | Clear solution | Clear solution | Clear solution |
| | Appearance 07.05.97 −5° C. | P in brown solution | Clear solution | Clear solution | Very little P | Clear solution |
| | Appearance 07.05.97 4° C. | P in brown solution | Clear solution | Clear solution | Very little P | Clear solution |
| | Appearance 07.05.97 25° C. | Clear solution | Clear solution | Clear solution | Clear solution | Clear solution |
| | Appearance 11.09.98 −5° C. | P in brown solution | Clear solution | Clear solution | Very little P | Clear solution |
| | Appearance 11.09.98 4° C. | P in brown solution | Clear solution | Clear solution | Clear solution | Clear solution |
| | Appearance 11.09.98 25° C. | Clear solution | Clear solution | Clear solution | Clear solution | Clear solution |
| | Appearance 13.03.98 −5° C. | P in brown solution | Clear solution | Clear solution | P in brown solution | Clear solution |
| | Appearance 13.03.98 4° C. | P in brown solution | Clear solution | Clear solution | Little P in brown solution | Clear solution |
| | Appearance 13.03.98 25° C. | Clear solution | Clear solution | Clear solution | Clear solution | Clear solution |
| | Appearance 13.03.98 40° C. | Clear solution | Clear solution | Clear solution | Clear solution | Clear solution |

| No. | 14.4.1997 | F | G | H | I |
|---|---|---|---|---|---|
| 1 | Carbendazim | 4.0 | 4.0 | 4.0 | 4.0 |
| 2 | Marlon AS 3 | 6.5 | 6.5 | 6.5 | 6.5 |
| 3 | Propylene glycol | 40.0 | 40.0 | 40.0 | 40.0 |
| 4 | Zonenfex | 1.0 | 1.0 | 1.0 | 1.0 |
| 5 | Kathon 893 | 17.0 | 17.0 | 17.0 | 17.0 |
| 6 | Benzyl alcohol | 10.0 | 15.0 | | |
| 7 | Dipropylene glycol | | | 10.0 | 15.0 |
| 8 | Propylene glycol | 21.5 | 16.5 | 21.5 | 16.5 |
| | Appearance 14.04.97 | Clear solution | Clear solution | Clear solution | Clear solution |
| | Appearance 07.05.97 −5° C. | Very little P | Clear solution | P | P |
| | Appearance 07.05.97 4° C. | Clear solution | Clear solution | P | P |
| | Appearance 07.05.97 25° C. | Clear solution | Clear solution | Clear solution | P |
| | Appearance 11.09.98 −5° C. | Little P | Clear solution | P | P |
| | Appearance 11.09.98 4° C. | Very little P | Clear solution | P | P |
| | Appearance 11.09.98 25° C. | Clear solution | Clear solution | Clear solution | Clear solution |
| | Appearance 13.03.98 −5° C. | Little P | Clear solution | P | P |
| | Appearance 13.03.98 4° C. | Very little P | Clear solution | P | P |
| | Appearance 13.03.98 25° C. | Clear solution | Clear solution | Clear solution | Clear solution |
| | Appearance 13.03.98 40° C. | Clear solution | Clear solution | Clear solution | Clear solution |

-continued

| No. | 14.4.1997 | J | K | L | M | N | O |
|---|---|---|---|---|---|---|---|
| 1 | Carbendazim | 4.0 | 4.0 | 4.0 | 4.0 | 4.0 | 4.0 |
| 2 | Marlon AS 3 | 6.5 | 6.5 | 6.5 | 6.5 | 6.5 | 6.5 |
| 3 | Propylene glycol | 40.0 | 40.0 | 40.0 | 40.0 | 40.0 | 40.0 |
| 4 | Zonenfex | 1.0 | 1.0 | 1.0 | 1.0 | 1.0 | 1.0 |
| 5 | Kathon 893 | 17.0 | 17.0 | 17.0 | 17.0 | 17.0 | 17.0 |
| 6 | Diethylene glycol butyl ether | 10.0 | 15.0 | | | | |
| 7 | 1-Methoxy-2-propanol | | | 10.0 | 15.0 | | |
| 8 | Polyglycol 400 | | | | | 10.0 | 15.0 |
| 9 | Propylene glycol | 21.5 | 16.5 | 21.5 | 16.5 | 21.5 | 16.5 |
| | Appearance 14.04.97 | Clear solution | Clear solution | Clear solution | Clear solution | Clear solution | Clear solution |
| | Appearance 07.05.97 −5° C. | P | P | P | P | P | P |
| | Appearance 07.05.97 4° C. | P | Little P | P | P | P | P |
| | Appearance 07.05.97 25° C. | Clear solution | Clear solution | Clear solution | Clear solution | Clear solution | Clear solution |
| | Appearance 11.09.98 −5° C. | P | P | P | P | P | P |
| | Appearance 11.09.98 4° C. | P | Little P | P | P | P | P |
| | Appearance 11.09.98 25° C. | Clear solution | Clear solution | Clear solution | Clear solution | Clear solution | Clear solution |
| | Appearance 13.03.98 −5° C. | P | P | P | P | P | P |
| | Appearance 13.03.98 4° C. | P | Little P | P | P | P | P |
| | Appearance 13.03.98 25° C. | Very little P | Very little P | Clear solution | Clear solution | Clear solution | Clear solution |
| | Appearance 13.03.98 40° C. | Clear solution | Clear solution | Clear solution | Clear solution | Clear solution | Clear solution |

Result: Suitable stabilizers for increasing the low-temperature stability of preservatives and low-water, carbendasulf-containing preparations are benzyl alcohol, phenoxyethanol and phenoxypropanols.

The following stabilizers are unsuitable: diethylene glycol butyl ether, 1-methoxy-2-propanol, polyglycol 400 and dipropylene glycol.

EXAMPLE 3

Content Determination

Background: The preparations according to the invention are purer (lower proportion of decomposition products) and the preparation is more economical than that which was previously possible. The preparation to date requires that the mixture be heated at +85° C. for 4 hours (if the residence time is shorter, the product is insufficiently stable or stable at low temperatures), which leads to the formation of byproducts.

According to the invention, a lower reaction temperature and/or reaction time of significantly less than 1 hour (preferably less than 30 minutes) is sufficient. The components carbendazim and Marlon AS 3 acid have only to be heated in a suitable solvent (e.g. 1,2-propylene glycol) to clear solubility, then cooled and mixed with the other formulation constituents. The carbendasulf solutions according to the invention are inevitably purer (and because of the higher carbendasulf content, more effective) and more economical to prepare.

| Formulation (see Example 2) | Carbendasulf |
|---|---|
| B | 3.72% |
| E | 3.68% |
| G | 3.58% |

-continued

| For comparison, contents of a number of production batches without the stabilizer according to the invention (formulation A) | |
|---|---|
| A1 | 3.19% |
| A2 | 3.26% |
| A3 | 3.50% |
| A4 | 3.43% |
| A5 | 3.42% |

In the case of formulations B, E and G, the carbendasulf content is generally higher than in the case of the production batches without the stabilizer according to the invention (formulation A).

EXAMPLE 4

Preservative Containing 12.5% of Phenoxypropanols

| Preparation of 3 kg on 03.06.98 | | |
|---|---|---|
| 1. | 4.0% | Carbendazim |
| 2. | 6.5% | Marlon AS 3 |
| 3. | 40.0% | Propylene glycol |
| 4. | 1.0% | Zonenfex (salt-containing mixture of 5-chloro- and N-methylisothiazolone) |
| 5. | 17.0% | Kathon 893 |
| 6. | 12.5% | Phenoxypropanols |
| 7. | 19.0% | Propylene glycol |

Carbendazim, Marlon AS 3 and propylene glycol were combined and heated to 85° C., the mixture was left to cool to 60° C. and the remaining ingredients were added (the temperature drops to <40° C.). The mixture was clear, greenish-brown and was filtered. The sample was stored and seeded at −5° C. or 4° C. or 25° C. or 40° C. Further data are given in the table below:

| | % (w/w) 24.09.98 |
|---|---|
| Carbendazim/-sulph | 3.8081 |
| 2-Aminobenzimidazole | |
| 2-N-Octyl-4-isothiazolin-3-one | 7.71 |
| 5-Chloro-2-methyl-4-isothiazolin-3-one | 0.1075 |
| Appearance 03.08.98 | Clear, greenish-brown solution |

-continued

| | % (w/w) 24.09.98 |
|---|---|
| Density (20° C.) in g/cm$^3$ | 1.051 |
| Refractive index $n_d$ | 1.4815 |
| pH (0.2% in demin. water) | 4.3 |
| Viscosity according to DIN 53121 | 20 |
| Efflux time DIN beaker 4 mm in s | |
| Hazen colour number, 04.08.98 | 322 |
| Gardner colour number, 04.08.98 | 2.4 |

Comparison, the preservative without stabilizer stored at −5° C., 4° C., 25° C.

| | −5° C. | Without stabilizer (−5° C.) | 4° C. |
|---|---|---|---|
| Appearance 08.07.98 | A few crystals at the bottom of a yellow solution: (base not covered, crystals only here and there) | Crystals on the bottom (about 10% of the volume) of an orange-yellow solution | Clear, yellow solution |
| Appearance 08.09.98 at storage temperature | Crystalline precipitate at the bottom of a yellow-orange solution: a few crystals at the edge | Considerable crystalline precipitate at the bottom (about 23% of the volume) of a yellow-orange solution: a layer of crystals about 20 mm in size on the surface | Clear, yellow-orange solution |
| Appearance 08.09.98 at room temperature | Crystalline precipitate at the bottom of a yellow-orange solution | Considerable crystalline precipitate at the bottom (about 25% of the volume) of a yellow-orange solution | |
| Density (20° C.) in g/cm$^3$ 08.09.98 | 1.051 | | 1.0513 |
| Refractive index $n_d$ 08.09.98 | 1.4803 | | 1.4500 |
| pH (0.2% in demin. water) | 3.8 | | 3.7 |
| Gardner colour number, 04.08.98 | 3.8 | | 3.4 |
| Appearance 01.07.99 at storage temperature | Crystalline precipitate at the bottom of a yellow-orange solution: a few crystals at the edge. Layer of crystals on the surface | Considerable crystalline precipitate at the bottom (about 25% of volume) of an orange solution | Clear, yellow-orange solution |
| Appearance 01.07.99 at room temperature | Crystalline precipitate at the bottom of a yellow-orange solution | Considerable crystalline precipitate at the bottom (about 25% of volume) of an orange solution | |
| Density (20° C.) in g/cm$^3$ 01.07.99 | 1.0502 | | 1.0517 |
| Refractive index $n_d$ 01.07.99 | 1.4598 | | 1.4587 |
| pH (0.2% in demin. water) | 4.2 | | 4.3 |
| Gardner colour number, 01.07.99 | 3.2 | | 3.4 |
| Appearance 08.07.98 | A few crystals at the bottom of a yellow solution: (base not covered, crystals only here and there) | Crystals on the bottom (about 10% of the volume) of an orange-yellow solution | Clear, yellow solution |
| Appearance 08.09.98 at storage temperature | Crystalline precipitate at the bottom of a yellow-orange solution: a few crystals at the edge | Considerable crystalline precipitate at the bottom (about 23% of the volume) of a yellow-orange solution: a layer of crystals about 20 mm in size on the surface | Clear, yellow-orange solution |
| Appearance 08.09.98 at room temperature | Crystalline precipitate at the bottom of a yellow-orange solution | Considerable crystalline precipitate at the bottom (about 25% of the volume) of a yellow-orange solution | |

-continued

|  | -5° C. | Without stabilizer (-5° C.) | 4° C. |
|---|---|---|---|
| Density (20° C.) in g/cm³ 08.09.98 | 1.051 |  | 1.0513 |
| Refractive index $n_d$ 08.09.98 | 1.4803 |  | 1.4500 |
| pH (0.2% in demin. water) | 3.8 |  | 3.7 |
| Gardner colour number, 04.08.98 | 3.8 |  | 3.4 |
| Appearance 01.07.99 at storage temperature | Crystalline precipitate at the bottom of a yellow-orange solution: a few crystals at the edge. Layer of crystals on the surface | Considerable crystalline precipitate at the bottom (about 25% of volume) of an orange solution | Clear, yellow-orange solution |
| Appearance 01.07.99 at room temperature | Crystalline precipitate at the bottom of a yellow-orange solution | Considerable crystalline precipitate at the bottom (about 25% of volume) of an orange solution |  |
| Density (20° C.) in g/cm³ 01.07.99 | 1.0502 |  | 1.0517 |
| Refractive index $n_d$ 01.07.99 | 1.4598 |  | 1.4587 |
| pH (0.2% in demin. water) | 4.2 |  | 4.3 |
| Gardner colour number, 01.07.99 | 3.2 |  | 3.4 |

EXAMPLE 5

Testing the Compatibility of the Preservative without Stabilizer (Stabilizer Replaced by Propylene Glycol) or Containing 12.5% of Phenoxypropanol (Example 4) in 5 Ubatol Polymer Dispersions (Pure Acrylate or Styrene Acrylate or Vinyl Acetate/Maleate Copolymer, Including One Salt-Sensitive Dispersion)

The biocides were added to the dispersions in an amount of 2%. This high concentration was knowingly chosen in order to see the effect of the preservative more clearly.

Result: After the biocides had been incorporated into four different salt-insensitive dispersion products, no incompatibility was found. All of the mixtures were stable upon storage. The odour and colour of the products were not changed by the preservatives according to the invention. A change in the minimum film-forming temperature (MFT) or the washfastness by the solvent content present in the variant is not evident either.

Both versions of the preservative without stabilizer are compatible with the standard dispersions tested. The incompatibility with the salt-sensitive dispersion has hitherto also been observed in the case of all other similar biocides (because of its specific monomer composition, this dispersion tolerates only salt-free biocides).

EXAMPLE 6

Preservative from 20.02.97 Addition of Phenoxyethanol

Carbendazim, Marlon AS 3 and propylene glycol (constituents 1 to 3; see table) were heated to 85° C. with stirring. After this temperature had been reached, (very little insoluble matter). The filtrate was combined with the mixture of constituents 4 to 7 (see table) and stirred for about ¼ of an hour. After seeding, the samples were stored in clear glass at -5° C., 4° C., 25 and 40° C.

| No. | 20.02.1997 | P | Q | R |
|---|---|---|---|---|
| 1 | Carbendazim | 4.0 | 4.0 | 4.0 |
| 2 | Marlon As 3 | 6.5 | 6.5 | 6.5 |
| 3 | Propylene glycol | 40.0 | 40.0 | 40.0 |
| 4 | Zonenfex | 1.0 | 1.0 | 1.0 |
| 5 | Kathon 893 | 17.0 | 17.0 | 17.0 |
| 6 | Phenoxyethanol |  | 10.0 | 20.0 |
| 7 | Propylene glycol | 31.5 | 21.5 | 11.5 |
|  | Appearance 20.02.97 | Clear, brown-yellow solution | Clear solution | Clear solution |
|  | Appearance 27.02.97 -5° C. | P in brown-yellow solution | Clear solution | Clear solution |
|  | Appearance 27.02.97 4° C. | P in brown-yellow solution | Clear solution | Clear solution |
|  | Appearance 27.02.97 25° C. | Very little P in brown-yellow solution | Clear solution | Clear solution |
|  | Appearance 27.02.97 40° C. | Clear, brown-yellow solution | Clear solution | Clear solution |
|  | Appearance 31.03.99 -5° C. | Considerable P in brown-yellow solution | Clear solution | Clear solution |
|  | Appearance 31.03.99 4° C. | Considerable P in brown-yellow solution | Clear solution | Clear solution |
|  | Appearance 31.03.99 25° C. | Very little P in brown-yellow solution | Clear solution | Clear solution |
|  | Appearance 31.03.99 40° C. | Clear, brown-yellow solution | Clear solution | Clear solution |
|  | Appearance 31.03.99 -5° C. | Considerable P in brown-yellow solution | Clear solution | Clear solution |
|  | Appearance 31.03.99 4° C. | Considerable P in brown-yellow solution | Clear solution | Clear solution |
|  | Appearance 31.03.99 25° C. | Very little P in brown-yellow solution | Clear solution | Clear solution |
|  | Appearance 31.03.99 40° C. | Clear, brown-yellow solution | Clear solution | Clear solution |

At room temperature, all solutions were clear, yellow-brownish. Storage was in clear glass at -5° C. or 4° C. or 25° C. or 40° C.

Result: After about 30 months at -5° C. or 4° C., the mixtures have the following precipitate percentages:

|   | −5° C. % P | +4° C. % P | Solvent addition |
|---|---|---|---|
| P | 50% | 40% | 1,2-Propylene glycol |
| Q | <5% | <1% | 10% of phenoxyethanol |
| R | 0% | Trace | 20% of phenoxyethanol |

Result: An addition of phenoxyethanol significantly improves the low-temperature stability of the preservative (formulation P).

EXAMPLE 7

Preservative from 21.07.99 Preparation and Stability of Comparatively Concentrated Carbendasulf Solutions (without PLG)

The solvent was initially introduced. Carbendazim and Marlon AS 3 were added thereto and stirred. The mixture heated up to 37° C. It was heated to about 80° C., giving a clear, brown solution. The solution was stirred until it had cooled to room temperature. The solution was then filtered with suction over a glass filter with a black belt filter.

Carbendasulf is prepared from carbendazim (black belt filter) and Marlon AS 3 in the ratio 1 mol:1 mol.

The 20% strength and 10% strength solutions were prepared from a more highly concentrated solution by dilution. The individual solutions were seeded with crystals. These solutions were stored in each case at −5° C., 4° C. and 25° C. in clear glass in order to establish the low-temperature stability.

Result: The combination of carbendasulf with stabilizers according to the invention permits the preparation of comparatively highly concentrated carbendasulf solutions, which can be combined with further active ingredients to give broad-activity, sometimes synergistically effective, preparations.

EXAMPLE 8

Preservative from 20.07.99 Preparation and Stability of Comparatively Concentrated Carbendasulf Solutions (with PLG)

1,2-Propylene glycol was initially introduced, carbendazim and Marlon AS 3 were added thereto and the mixture was stirred. The mixture heated up to 45° C. and became paste-like. It was heated to about 80° C., forming a clear brown solution. The stabilizer was then added. The solution was stirred until it had cooled to room temperature. The solution was then filtered with suction over a glass filter with black belt filter.

Carbendasulf is prepared from carbendazim and Marlon AS 3 in the ratio 1 mol:1 mol.

The 20% strength and 10% strength solutions were prepared by dilution. The individual solutions were seeded with crystals. The solutions were each stored in clear glass at −5° C., 4° C., 25° C. in order to establish the low-temperature stability. The data are given in the table below.

|   | Sample | | | | | | | |
|---|---|---|---|---|---|---|---|---|
|   | I | II | III | IV | V | VI | VII | VIII |
| Carbendasulf | 20% | 10% | 20% | 10% | 20% | 10% | 20% | 10% |
| Phenoxyethanol | 80% | 90% |   |   |   |   |   |   |
| 3-Phenylpropanol, Merck |   |   | 80% | 90% |   |   |   |   |
| Benzyl alcohol |   |   |   |   | 80% | 90% |   |   |
| Phenoxypropanols |   |   |   |   |   |   | 80% | 90% |
| Appearance on 21.07.99 | Yellow-brown clear solution | Yellow-brown clear solution | Yellow-brown clear solution | Yellow-brown clear solution | Red-brown clear solution | Red-brown clear solution | Yellow-brown clear solution | Yellow brown clear solution |
| Appearance at the storage temperature of −5° C. on 28.07.99 | Solid, brown substance | Solid, pale brown substance | Solid, brown-yellow substance | Yellow-brown clear solution | Red-brown clear solution | Red-brown clear solution | Solid, brown-yellow substance | Solid, brown-yellow substance |
| Appearance at the storage temperature of −5° C. on 28.07.99 at room temperature | Yellow-brown clear solution | Yellow-brown clear solution | Yellow-brown clear solution | Yellow-brown clear solution | Red-brown clear solution | Red-brown clear solution | Yellow-brown clear solution | Yellow-brown clear solution |
| Appearance at the storage temperature of 4° C. on 28.07.99 | Yellow-brown clear solution | Yellow-brown clear solution | Yellow-brown clear solution | Yellow-brown clear solution | Red-brown clear solution | Red-brown clear solution | Yellow-brown clear solution | Yellow-brown clear solution |
| Appearance at the storage temperature of 4° C. on 28.07.99 at room temperature | Yellow-brown clear solution | Yellow-brown clear solution | Yellow-brown clear solution | Yellow-brown clear solution | Red-brown clear solution | Red-brown clear solution | Yellow-brown clear solution | Yellow-brown clear solution |
| Appearance at the storage temperature of 25° C. on 28.07.99 | Yellow-brown clear solution | Yellow-brown clear solution | Yellow-brown clear solution | Yellow-brown clear solution | Red-brown clear solution | Red-brown clear solution | Yellow-brown clear solution | Yellow-brown clear solution |

|  | Sample | | | | | | | |
|---|---|---|---|---|---|---|---|---|
|  | IX | X | XI | XII | XIII | XIV | XV | XVI |
| Carbendasuif | 20% | 10% | 20% | 10% | 20% | 10% | 20% | 10% |
| 1,2-Propylene glycol | 23.33% | 11.67% | 23.33% | 11.67% | 23.33% | 11.67% | 23.33% | 11.67% |
| Phenoxyethanol | 56.67% | 78.33% |  |  |  |  |  |  |
| 3-Phenylpropanol, Merck |  |  | 56.67% | 78.33% |  |  |  |  |
| Benzyl alcohol |  |  |  |  | 56.67% | 78.33% |  |  |
| Phenoxypropanols |  |  |  |  |  |  | 56.67% | 78.33% |
| Appearance on 20.07.99 | Clear solution | Clear solution | Clear solution | Clear solution | Clear solution | Clear solution | Clear solution | Clear solution |
| Appearance at the storage temperature of 5° C. on 28.07.99 | Clear solution | Clear solution | Crystallized | Clear solution | Clear solution | Clear solution | Clear solution | Solution |
| Appearance at the storage temperature of −5° C. on 28.07.99 at room temperature | Clear solution | Clear solution | Clear solution | Clear solution | Clear solution | Clear solution | Clear solution | Clear solution |
| Appearance at the storage temperature of 4° C. on 28.07.99 | Clear solution | Clear solution | Clear solution | Clear solution | Clear solution | Clear solution | Clear solution | Clear solution |
| Appearance at the storage temperature of 4° C. on 28.07.99 at room temperature | Clear solution | Clear solution | Clear solution | Clear solution | Clear solution | Clear solution | Clear solution | Clear solution |
| Appearance at the storage temperature of 25° C. on 28.07.99 | Clear solution | Clear solution | Clear solution | Clear solution | Clear solution | Clear solution | Clear solution | Clear solution |

Result: The combination of carbendasulf with stabilizers according to the invention permits the preparation of comparatively highly concentrated carbendasulf solutions, which can be combined with further active ingredients to give broad-activity, sometimes synergistically active, preparations.

Carbendasulf solutions with a combination of aliphatic glycols or glycol ethers and stabilizers according to the invention are preferred.

EXAMPLE 9

Preparation of a Stable 20% Strength Carbendasulf Solution with Phenoxyethanol 7.45% of carbendazim+12.55% of Marlon AS 3 acid+23.33% of propylene glycol (PLG)+56.67% of phenoxyethanol (POE).

Propylene glycol was initially introduced, the carbendazim was added and, with stirring, Marlon AS 3 was added. The mixture becomes solid and heats up to 45° C. The mixture was heated to 80° C., and the now liquid preparation was admixed with phenoxyethanol and, with stirring, allowed to cool to room temperature, giving a clear brown solution.

EXAMPLE 10

Compatibility of Benzisothiazolone BIT and Carbendasulf Solution

50% of 20% strength carbendasulf solution from Example 9 was combined with 10% of Proxel press paste (BIT) and 40% of phenoxyethanol and stirred for about 1 hour, giving a clear deep red solution.

EXAMPLE 11

Preservative from 5.8.99 Combination of BIT and Carbendasulf Solution

|  | A | B |
|---|---|---|
| Proxel press paste (77.3% of BIT) | 12.9 | 6.5 |
| Carbendasulf solution from Example 9 | 50.0 | 25.0 |
| Phenoxyethanol | 37.1 | 68.5 |

Appearance: all solutions were clear, red

The invention claimed is:

1. A liquid, low-temperature-stabilized preservative comprising carbendazim or a salt thereof and an effective amount of at least one low-temperature stabilizer selected from the group consisting of aromatic alcohols.

2. The preservative according to claim 1, wherein the low-temperature stabilizer is phenylpropanol or benzyl alcohol.

3. The preservative according to claim 2, wherein the preservative has at least 2% by weight of the low-temperature stabilizer.

4. The preservative according to claim 2, wherein said carbendazim or a salt thereof is a salt of carbendazim, which is an alkylbenzenesulfonate salt, where the alkyl group has 6 to 18 carbon atoms.

5. The preservative according to claim 2, wherein said preservative has at least 5% by weight of the low-temperature stabilizer.

6. The preservative according to claim 2, further comprising biocidal active ingredients.

7. The preservative according to claim 1, wherein the low-temperature stabilizer comprises 1-phenoxy-3-propanol, 1-phenoxy-2-propanol and/or phenoxyethanol.

8. The preservative according to claim 7, wherein the preservative has at least 2% by weight of the low-temperature stabilizer.

9. The preservative according to claim 7, wherein said carbendazim or a salt thereof is a salt of carbendazim, which is an alkylbenzenesulfonate salt, where the alkyl group has 6 to 18 carbon atoms.

10. The preservative according to claim 7, wherein said preservative has at least 5% by weight of the low-temperature stabilizer.

11. The preservative according to claim 1, wherein said preservative contains at least 2% by weight of the low-temperature stabilizer.

12. The preservative according to claim 11, wherein said carbendazim or a salt thereof is a salt of carbendazim, which is an alkylbenzenesulfonate salt, where the alkyl group has 6 to 18 carbon atoms.

13. The preservative according to claim 11, wherein said preservative has at least 5% by weight of the low-temperature stabilizer.

14. The preservative according to claim 1, wherein said carbendazim or a salt thereof is a salt of carbendazim, which is an alkylbenzenesulfonate salt, where the alkyl group has 6 to 18 carbon atoms.

15. The preservative according to claim 14, wherein said preservative has at least 5% by weight of the low-temperature stabilizer.

16. The preservative according to claim 1, wherein said preservative has at least 5% by weight of the low-temperature stabilizer.

17. The preservative according to claim 1, further comprising biocidal active ingredients.

* * * * *